Figure 1:
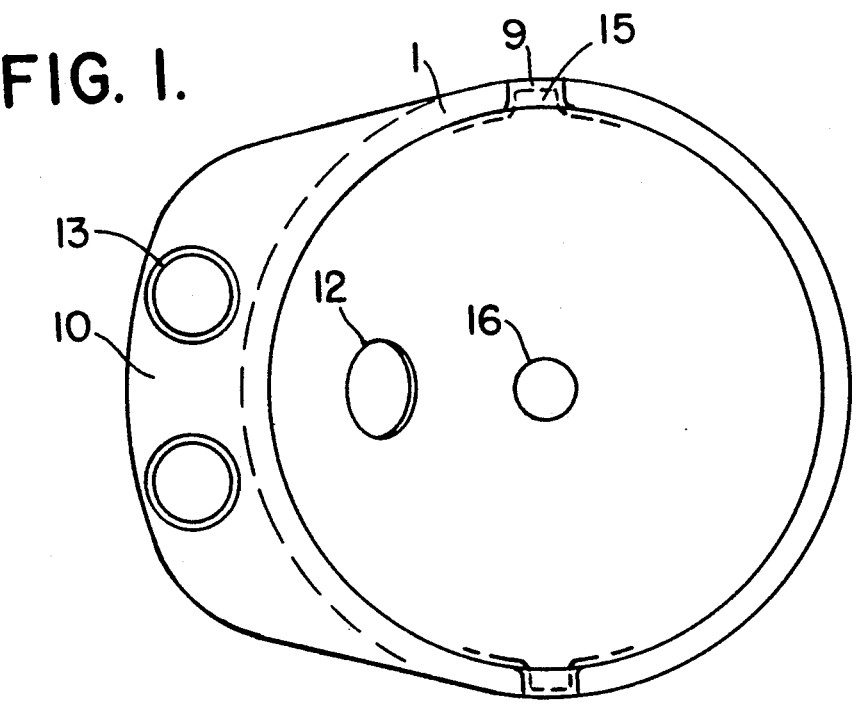

United States Patent [19]
Zeiler et al.

[11] Patent Number: 5,108,447
[45] Date of Patent: Apr. 28, 1992

[54] ARTIFICIAL ACETABULUM

[75] Inventors: Gunther Zeiler, Rummelsberg, Fed. Rep. of Germany; Johann U. Steiger, Meilen, Switzerland; Rudolf Koch, Berlingen, Switzerland; Jurg Oehy, Winterthur, Switzerland

[73] Assignee: Sulzer Brothers Limited, Winterthur, Switzerland

[21] Appl. No.: 662,341

[22] Filed: Feb. 28, 1991

[30] Foreign Application Priority Data

Mar. 2, 1990 [CH] Switzerland .................. 00669/90

[51] Int. Cl.[5] ............................................. A61F 2/32
[52] U.S. Cl. ............................................ 623/22; 623/16; 623/23
[58] Field of Search .................... 623/16, 18, 22, 23

[56] References Cited

U.S. PATENT DOCUMENTS

| | | | |
|---|---|---|---|
| 3,584,318 | 1/1966 | Scales et al. | 623/22 |
| 4,695,282 | 9/1987 | Forte et al. | 623/22 |
| 4,822,369 | 4/1989 | Oueveau et al. | 623/22 |

FOREIGN PATENT DOCUMENTS

| | | | |
|---|---|---|---|
| 0190093 | 8/1986 | European Pat. Off. | |
| 0298234 | 1/1989 | European Pat. Off. | 623/22 |
| 0308297 | 3/1989 | European Pat. Off. | |
| 0341199 | 11/1989 | European Pat. Off. | 623/22 |
| 2617040 | 12/1988 | France | |
| 2622432 | 5/1989 | France | 623/22 |

Primary Examiner—David J. Isabella
Assistant Examiner—Gualtieri Gina
Attorney, Agent, or Firm—Kenyon & Kenyon

[57] ABSTRACT

An artificial acetabulum has a thin metallic outer shell and a relatively thick metallic inner shell which is secured to the outer shell via a damping ring located at the peripheral edges of the shells. The outer shell has a thickness of less than one-fifth of the thickness of the inner shell to compensate for stresses in the direction of the osseous tissue during the transfer of force peaks. A centering pin is provided on the inner shell and an annular shoulder is provided on the outer shell about the centering pin to provide further elastic damping of forces transmitted between the shells.

7 Claims, 1 Drawing Sheet

ARTIFICIAL ACETABULUM

This invention relates to an artificial acetabulum. More particularly, this invention relates to a multi-component acetabulum.

As is known, if metallic acetabula are constructed as double shells, this is normally to enable an attachment of an outer shell in osseous tissue without impairing the loadbearing spherical surface of an inner shell for a spherical head or without having to combine the material properties with respect to wear and auxiliary motion in one part with the suitability of the osseous tissue for fusion.

Similar considerations also apply with respect to acetabula having a plastic inner shell such as described in U.S. Pat. No. 4,624,674 where, in addition, a spherical head is enclosed in the inner casing by dividing the inner casing and by attaching this together in the outer casing by a snap fit.

In all of these applications, the rigidity of the shells is chosen so as to be great enough for high non-deformability to be achieved with respect to the spherical head in order to obtain the desired anti-friction properties. However, the rigid shell has the disadvantage of not being able to follow long-term small changes in the supporting osseous tissue and in not being able to transmit load surges without dampening.

Other types of multi-component acetabula have also been known from U.S. Pat. No. 4,822,369, French Patent Application 2,617,040 and European Patent Applications 0,190,093; 0,308,297; and 0,341,199.

It is an object to the invention to create an artificial acetabulum with which the outer contours can follow small changes in the supporting osseous tissue and which is responsible for load compensation in the direction of the osseous tissue.

It is another object of the invention to provide a multi-component, artificial acetabulum which permits an outer shell to follow slight alterations in osseous tissue during implantation.

It is another object of the invention to provide an artificial acetabulum with an elastic outer shell to compensate for stresses in the direction of osseous tissue during the transfer of force surges.

It is another object to the invention to elastically damp forces imposed on an acetabulum.

Briefly, the invention provides an artificial acetabulum which is comprised of a thin metallic outer shell for implanting in a bone, a metallic inner shell within the outer shell for receiving a joint head and which is spaced from the outer shell to define a gap therebetween, and a damping ring secured to and between an outer edge of the inner shell and the outer shell in order to elastically support the inner shell in the outer shell.

The thin outer shell is also provided with a bore which is disposed on a central axis of the shell, while the inner shell has a centering pin projecting into the bore of the outer shell.

The relative thickness of the shells is such that the outer shell is of a thickness less than one-fifth of the thickness of the inner shell.

In order to accommodate mounting of the damping ring, the outer shell is provided with an internally disposed annular groove to receive the ring. In addition, at least one of the outer shell and the damping ring has a conical surface to facilitate insertion of the ring into the groove of the outer shell.

The advantage of the acetabulum is such that the attachment between the acetabulum and osseous tissue is maintained regardless of small changes in the tissue over the entire fused outer shell and that with sudden loads on the spherical head of the femoral prosthesis, one part of the load peak or surge is reduced by the shells during transfer to the osseous tissue.

Figure 2:
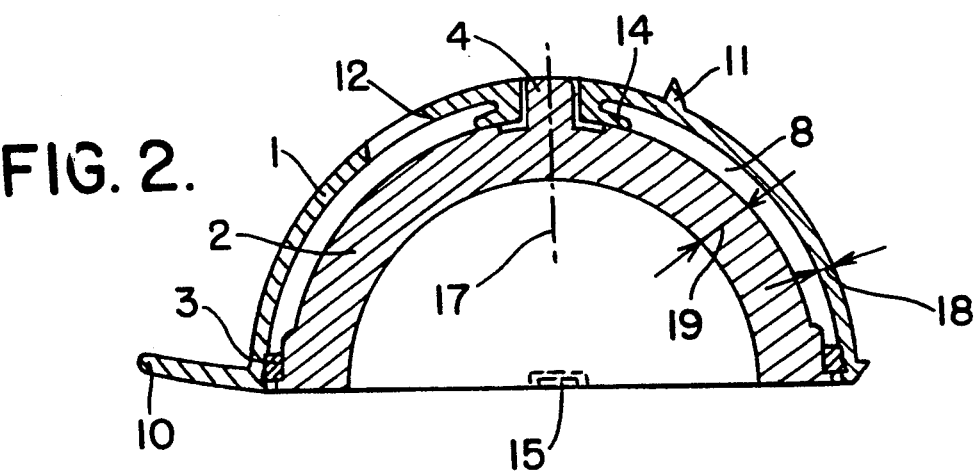
Figure 3:
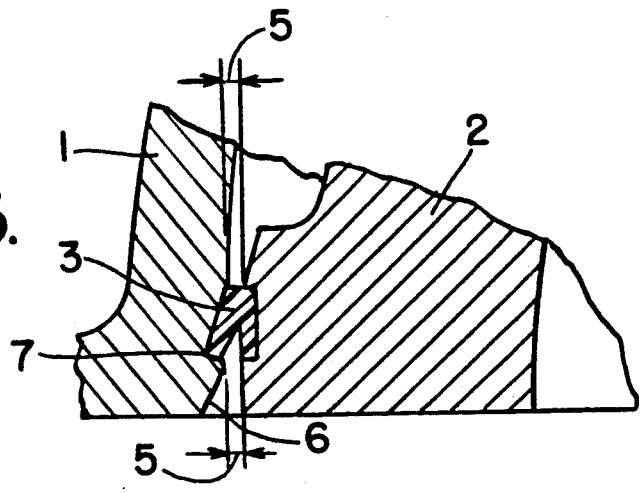

These and other objects and advantages of the invention will become more apparent from the following detailed description taken in conjunction with the accompanying drawings wherein:

FIG. 1 illustrates a view into the socket of an outer shell of an acetabulum constructed in accordance with the invention; and FIG. 2 illustrates a cross-sectional view of an acetabulum constructed in accordance with the invention; and FIG. 3 illustrates an enlarged detail of a longitudinal section through the assembled shells and damping ring in accordance with the invention.

Referring to FIG. 2, the artificial acetabulum has a thin metallic outer shell 1 for implanting in a bone and a thicker metallic inner shell 2 within the outer shell 1 for receiving a spherical head (not shown) and which is spaced from the outer shell to define a gap 8 therebetween. The outer shell 1 has a lateral flange 10 at the peripheral edge of the shell 1 and is provided with suitable attachment means for attaching to osseous tissue, for example means in the form of a spike 11 and bone screws (not shown) which may pass through holes 12, 13 in the shell 1 and flange 10, respectively. In addition, the outer shell 1 has a bore 16 disposed on a central axis 17.

The inner shell 2 has a centering pin 4 which projects into the bore 16 of the outer shell 1 for centering purposes during the assembly of the acetabulum. In addition, the outer shell 1 is provided with an internally disposed annular shoulder 14 about the bore 16 which is disposed in contact with the inner shell 2 about the centering pin 4.

As illustrated in FIG. 2, the annular shoulder 14 abuts the inner shell 2 circumferentially about an annular recess in the inner shell 2 concentric to the centering pin 4 and central axis 17 of the inner shell 1. The annular shoulder 14 is shaped to flex towards the outer shell 2 when the two shells 1, 2 are forced together so that a damping effect can be obtained against local surges.

As shown in FIG. 2, the outer shell 1 is of a thickness 18 which is less than the thickness 19 of the inner shell 2. For example, the outer shell 1 is of a thickness less than one-fifth of the thickness of the inner shell 2.

As also indicated in FIG. 2, a damping ring 3 is secured to and between the outer edge of the inner shell 2 and the outer shell 1 in order to elastically support the inner shell 2 in the outer shell 1.

Referring to FIG. 3, a small radial clearance 5 is provided between the outer peripheral edge of the inner shell 2 and the inner peripheral edge of the outer shell 1 across which the damping ring 3 extends. In addition, the outer ring 1 is provided with an internally disposed annular groove 7 which receives the elastic damping ring 3 while the inner ring 2 has a groove seating the ring 3 in place. Further, the outer shell 1 is provided with a conical surface 6 to facilitate insertion of the ring 3 into the groove 7. Likewise, the damping ring 3 can be provided with an exterior conical surface to facilitate insertion into the outer shell 1.

Referring to FIG. 1, for protection against torsion, s the outer shell 1 is provided with a pair of notches 9 which are diametrically disposed 180° from each other at the peripheral edge of the shell 1. In addition, the inner shell 2 is provided with protrusions 15 which are sized to project into the notches 9. With respect to the axis 17 of the outer shell 1, the protrusions 15 are spaced from the sides of the notches 9 With a clearance of a size of the radial clearance 5 tangentially and axially to the notches.

The metallic outer shell 1 is kept thin enough so as to adapt elastically to small changes in the osseous tissue after fusion in the osseous tissue. Further, forces from the relatively rigid inner shell 2 are only transferred to the outer shell 1 which is deformed according to the forces of reaction in the osseous tissue and according to the rigidity of the outer shell 1. These forces are transmitted through the centering pin 4 and the shoulder 14 in the region of the pole of the outer shell 1 and by the damping ring 3 in the region of the shell edges. With the deformation of the outer shell 1, pressure peaks are avoided and the stresses are compensated over a larger surface area between the osseous tissue and the outer shell 1.

Generally, the damping ring 3 is provided already mounted in the inner ring 2 prior to a surgical procedure. After the outer shell 1 has been implanted, the inner shell 2 can be inserted into the outer shell 1. To this end, the centering pin 4 is guided in the centering bore 16 along the axis 17 of the outer shell 1 until the damping ring 3 engages in the groove 7 of the outer shell 1 and the inner shell 2 is supported on the shoulder 14 of the outer shell 1. During assembly, the elastic damping ring 3 is passed via the conical surface 6 on the outer shell 1 before snapping into the groove 7. In the assembled condition, the damping ring 3 is prestressed so as to transfer the normal loading forces without the radial clearance 5 between the shells 1, 2 being totally removed.

The alteration in the position of the outer shell 1 with respect to the inner shell 2 is made possible and, if required, is limited by the gap 8 between the two shells 1, 2.

In a preferred embodiment, the metallic outer shell 1 is made up titanium while the inner shell 2 is made up a cobalt alloy and the damping ring 5 made of polyethylene.

The invention thus provides an acetabulum which is able to damp load peaks which are imposed upon the acetabulum during use. Further, the acetabulum provides a thin outer shell which is able to deform so as to follow slight alterations in the osseous tissue. This thin elastic outer shell also compensates for stresses in the direction of the osseous tissue during the transfer of force peaks.

What is claimed is:

1. An artificial acetabulum comprising:
a thin metallic outer shell for implanting in a bone, said shell having a bore disposed on a central axis of said shell;
a metallic inner shell disposed within said outer shell for receiving a spherical joint head and being spaced from said outer shell to define a gap therebetween, said inner shell having a centering pin projecting into said bore of said outer shell and being of a greater thickness than said outer shell; and
a damping ring secured to and between an outer edge of said inner shell and said outer shell to elastically support said inner shell in said outer shell.

2. An acetabulum as set forth in claim 1 wherein said outer shell is of a thickness less than one-fifth of the thickness of said inner shell.

3. An acetabulum as set forth in claim 1 wherein said outer shell has an internally disposed annular shoulder extending outwardly about said bore and in contact with said inner shell.

4. An acetabulum as set forth in claim 1 wherein said outer shell has an internally disposed annular groove for receiving said ring.

5. An acetabulum as set forth in claim 4 wherein said outer shell and said dampening ring has a conical surface to facilitate insertion of said ring into said groove of said outer shell.

6. An acetabulum as set forth in claim 1 wherein said ring is made of polyethylene.

7. An acetabulum as set forth in claim 1 wherein said outer shell is made of titanium and said inner shell is made of a cobalt alloy.

* * * * *